Figure 1:
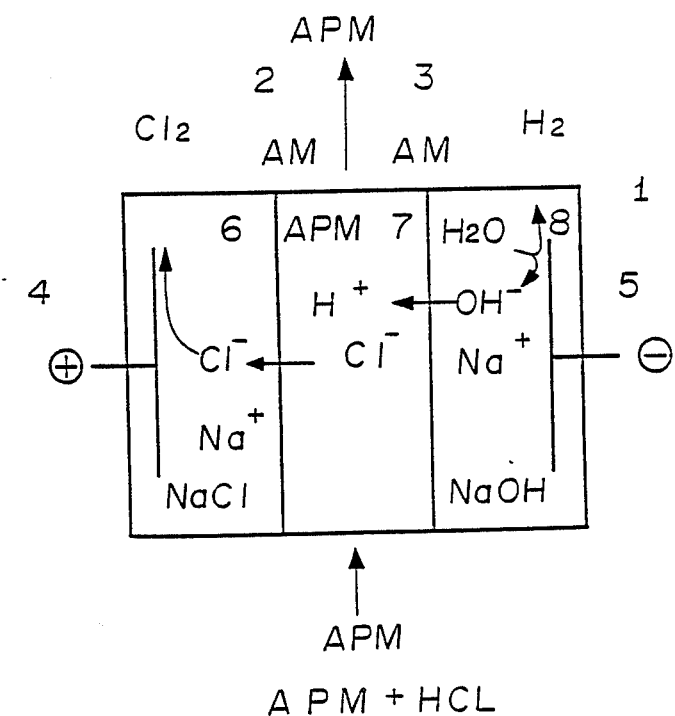

United States Patent [19]

Kurauchi et al.

[11] Patent Number: 4,944,852
[45] Date of Patent: * Jul. 31, 1990

[54] METHOD FOR PURIFYING A DIPEPTIDE ESTER

[75] Inventors: Yasuhiro Kurauchi; Michihiro Akazawa, both of Atsugi; Tsuneo Harada, Shin-nanyo; Kiyotaka Oyama, Hikari; Akira Tokuda, Shin-nanyo, all of Japan

[73] Assignee: Tosoh Corporation, Shin-nanyo, Japan

[*] Notice: The portion of the term of this patent subsequent to May 16, 2006 has been disclaimed.

[21] Appl. No.: 228,489

[22] Filed: Aug. 5, 1988

[30] Foreign Application Priority Data

Aug. 7, 1987 [JP] Japan ................... 62-196296

[51] Int. Cl.$^5$ ................................ B01D 15/00
[52] U.S. Cl. ..................... 204/131; 204/138; 204/182.6; 204/182.3
[58] Field of Search ............... 204/138, 182.6, 182.3, 204/130, 131

[56] References Cited

U.S. PATENT DOCUMENTS 4,830,720  5/1989  Harada et al. ................ 204/131

FOREIGN PATENT DOCUMENTS 58-55577  9/1983  Japan .
60-121288 12/1985  Japan .

OTHER PUBLICATIONS

Chem. Abstract, vol. 99, No. 12, Sep. 19, 1983, p. 495, No. 95856q, Columbus, Ohio, US; JP-A-5855 577 (Yuasa Battery Co.).
Chem. Abstract, vol. 103, No. 24, Dec. 16, 1985, p. 456, No. 202814z, Columbus Ohio, US; JP-A-60 121 288.
Chem. Abstract, vol. 108, No. 7, Feb. 15, 1988, p. 780, No. 56620t, Columbus Ohio, US; JP-A—62 153 298.
Chem. Abstract, vol. 95, No. 3, Jul. 20, 1981, p. 759, No. 25637n, Columbus, Ohio, US; DE-A-3 013 701.

Primary Examiner—John F. Niebling
Assistant Examiner—Arun S. Phasge
Attorney, Agent, or Firm—Oblon, Spivak, McClelland, Maier & Neustadt

[57] ABSTRACT

A method for purifying a dipeptide ester by electrolysis in an electrolytic cell comprising an anode compartment, a cathode compartment and a central compartment partitioned by anion exchange membranes, which comprises supplying an aqueous dipeptide ester solution containing an inorganic acid to the central compartment defined by said anion exchange membranes, an aqueous solution containing a basic substance or an aqueous electrolyte solution containing a basic substance to the cathode compartment and an aqueous electrolyte solution to the anode compartment, supplying hydroxyl ions from the cathode compartment to the central compartment through the anion exchange membrane to neutralize the aqueous dipeptide ester solution containing the inorganic acid and removing anions of the inorganic acid in the aqueous dipeptide ester solution from the central compartment to the anode compartment through the anion exchange membrane.

10 Claims, 3 Drawing Sheets

METHOD FOR PURIFYING A DIPEPTIDE ESTER

The present invention relates to a method for purifying a dipeptide ester. More particularly, it relates to a method for obtaining an aqueous solution of pure dipeptide ester by subjecting an aqueous dipeptide ester solution containing an inorganic acid to ion exchange electrolysis by means of anion exchange membranes to neutralize it and simultaneously remove anions from it. The method of the present invention is particularly useful for removing with high efficiency inorganic anions contained in the product in the production of α-L-aspartyl-L-phenylalanine methyl ester (hereinafter referred to simply as a-APM).

α-APM is a dipeptide ester composed of L-aspartic acid and L-phenylalanine, and it is expected to be a prospective sweetener as a substitute for sugar.

For its production, there have been proposed a chemical peptide synthesis and a biochemical method using an enzyme or a microorganism which produces it (e.g. Kiyotaka Koyama, Bioindustry, Vol 2, No. 9, p.5-11, 1985).

In most cases of the chemical peptide synthesis, not only desired α-APM but also its isomer β-APM is formed during the synthesis. This β-isomer has bitterness as is different from the α-isomer. Therefore, inclusion of the β-isomer reduces the commercial value of α-APM. In order to remove such β-APM, a method has been proposed in which an inorganic acid is added to impure APM in an aqueous solvent to form and separate a hardly soluble adduct of α-APM with the inorganic acid (Japanese Examined Patent Publication No. 41425/1974). As the biochemical method, a method has been proposed wherein an N-substituted aspartic acid and a phenylalanine lower alkyl ester are condensed in the presence of a proteolytic enzyme, and then the substituent is removed (Japanese Unexamined Patent Publication No. 43793/1983). In this case, no side reaction to form β-APM takes place, but a-L-asparatyl-L-phenylalanine (AP) and 3-benzyl-6-carboxymethyl-2,5-diketopiperazine (DKP) will be contained as inclusions by the reaction. In order to separate such inclusions, a method has been employed wherein the inclusions are brought in contact with a Cl type anion exchange resin so that they will be removed as adsorbed on this anion exchange resin (Japanese Examined Patent Publication No. 49199/1985). In this case, the inclusions are adsorbed on the ion exchange resin, and $Cl^{\ominus}$ ions formed by the ion exchange with DKP and AP will be eluted as a hydrochloride-type α-APM to the aqueous o -APM solution.

As described in the foregoing, in each case of the chemical synthesis and the biochemical synthesis, an inorganic acid is present as an impurity in α-APM.

In such a case, the subsequent step will be a step for the acid removal in order to obtain pure α-APM. Heretofore, in such acid removal step, it has been common to use an alkali metal hydroxide for neutralization and to obtain α-APM by crystallization. However, in this method of neutralization and crystallization, there have been problems such that α-APM is likely to be decomposed by alkali, and separated α-APM crystals include a salt formed by the neutralization.

Further, an ion exchange resin method or an electrodialysis method may be mentioned as a method for the removal of a salt from α-APM. However, in the electrodialysis method, α-APM containing an inorganic acid is required to be neutralized with an alkali metal hydroxide before subjecting it to electrodialysis. Further, the pH changes during the electrodialysis, and ionic APM tends to be retained in the ion exchange membrane, whereby the membrane resistance will increase. It may further happen that ionic APM leaks to electrode compartments, whereby the electrodes are damaged or noxious substances are produced.

On the other hand, in the ion exchange resin method, α-APM is likely to be adsorbed on the resin, thus leading to a decrease of the yield or a deterioration of the resin.

Further, in the dialysis by means of a porous membrane, leakage of α-APM through the membrane is substantial, thus leading to a poor yield.

In addition to the above, an electrolytic ion exchange method is known in the field of amino acid synthesis (Japanese Unexamined Patent Publication No. 55577/1983). In this process, the space between the anode and the cathode is devided by two or three hydrocarbon-type anion exchange membranes, and a hydrochloric acid solution of an amino acid is supplied to a central compartment defined by the anion exchange membranes, an aqueous solution of sodium hydroxide or potassium hydroxide is supplied to the cathode compartment and an aqueous solution of hydrochloric acid is supplied to the anode compartment, to conduct electrolytic ion exchange to obtain an amino acid solution.

This process is in principle effective for the purification of an amino acid, but involves an important problem. Namely, it is a problem with respect to the durability of the hydrocarbon-type anion exchange membrane. The hydrocarbon-type anion exchange membrane is usually poor in the durability against strong acid or strong alkali or under a high temperature condition. Further, in the presence of a strongly oxidative substance such as chlorine gas, the membrane has no substantial durability, and in an extreme case, the membrane is destroyed in a short period of time of about a few weeks.

Therefore, if it is attempted to practice such a process by using the conventional hydrocarbon-type anion exchange membrane, it will be necessary to frequently replace the ion exchange membrane, and consequently, the process itself will be cumbersome and economically disadvantageous.

As another important problem, the permeability of $H^+$ ions will be a serious problem when an aqueous solution of hydrochloric acid is used for the anode compartment. In general, the higher the concentration of the acid which is in contact with the anion exchange membrane is, the more readily the $H^+$ ions permeate through the anion exchange membrane.

Accordingly, in such a electrolytic process, when the anolyte is an acid solution, the reverse diffusion of $H^+$ ions from the anode compartment takes place as the acid concentration becomes high, whereby the $H^+$ ions transfer to the solution in the central compartment and react for neutralization with $OH^-$ transferred from the cathode compartment through the anion exchange membrane to form $H_2O$. Accordingly, the amount of $OH^-$ ions to be supplied for the electrolytic ion exchange will be decreased, and consequently, the current efficiency of the ion exchange substance will be decreased.

A further problem is that if the selectivity of the anion exchange membrane is inadequate, leakage of the ion exchange substance to the cathode and anode compartments is likely to take place.

As described in the foregoing, the process for purifying an amino acid by ion exchange electrolysis is a known technique and is strongly desired to be practically in use as an industrial process. Nevertheless, it has not yet been established as a satisfactory industrial process because of the restrictive conditions for the process and a number of problems to be solved.

Especially in the case of the purification of a dipeptide ester intended by the present invention, this dipeptide ester has a poor solubility in water, and it is therefore ideal to conduct the ion exchange electrolysis at a high temperature. However, the conventional hydrocarbon-type anion exchange membrane is poor in the durability at a high temperature, and it is obliged to conduct the electrolysis at a level of room temperature, whereby the yield in the purification of the dipeptide ester is substantially reduced. Further, the dipeptide ester is expensive as compared with an amino acid, and there is a concern about the economical disadvantage due to the leakage or due to the temperature condition for the electrolysis. Thus, there have been various problems in the application of the electrolytic ion exchange method to the purification of such dipeptide ester.

It is an object of the present invention to overcome the difficulties in the conventional electrolytic ion exchange method wherein an ion exchange membrane is employed and to provide a method whereby the inorganic acid in the dipeptide ester is readily and efficiently neutralized, and at the same time anions are removed by means of an efficient, economical electrolytic ion exchange method.

The present inventors have conducted extensive research on a method for purifying a dipeptide ester, particularly on the stability of the dipeptide ester and the leakage to the cathode and anode compartments, which are the problems of the electrolytic ion exchange method. As a result, they have found it possible to remove anions under a stable condition without leakage of the dipeptide ester by ion exchange electrolysis in an electrolytic cell wherein anion exchange membranes are used as diaphragms, by supplying an aqueous dipeptide ester solution containing an inorganic acid entered during the process for the production of the dipeptide ester, directly to a central compartment defined by the anion exchange membranes, an aqueous solution containing a basic substance or an aqueous electrolyte solution containing a basic substance to the cathode compartment and an aqueous electrolyte solution to the anode compartment. The present invention has been accomplished on the basis of this discovery.

The present invention provides a method for purifying a dipeptide ester by electrolysis in an electrolytic cell comprising an anode compartment, a cathode compartment and a central compartment partitioned by anion exchange membranes, which comprises supplying an aqueous dipeptide ester solution containing an inorganic acid to the central compartment defined by said anion exchange membranes, an aqueous solution containing a basic substance or an aqueous electrolyte solution containing a basic substance to the cathode compartment and an aqueous electrolyte solution to the anode compartment, supplying hydroxyl ions from the cathode compartment to the central compartment through the anion exchange membrane to neutralize the aqueous dipeptide ester solution containing the inorganic acid and removing anions of the inorganic acid in the aqueous dipeptide ester solution from the central compartment to the anode compartment through the anion exchange membrane.

Figure 2:
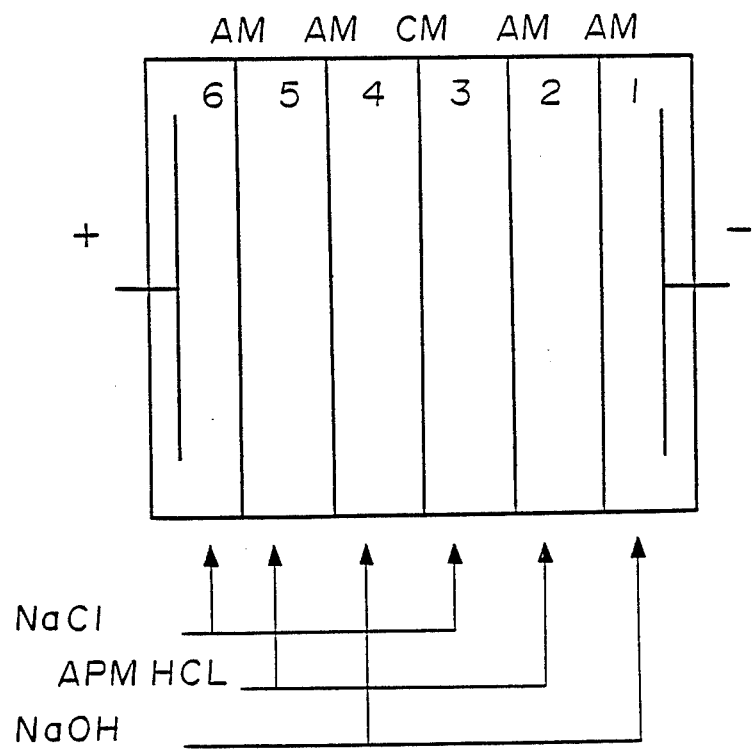
Figure 3:
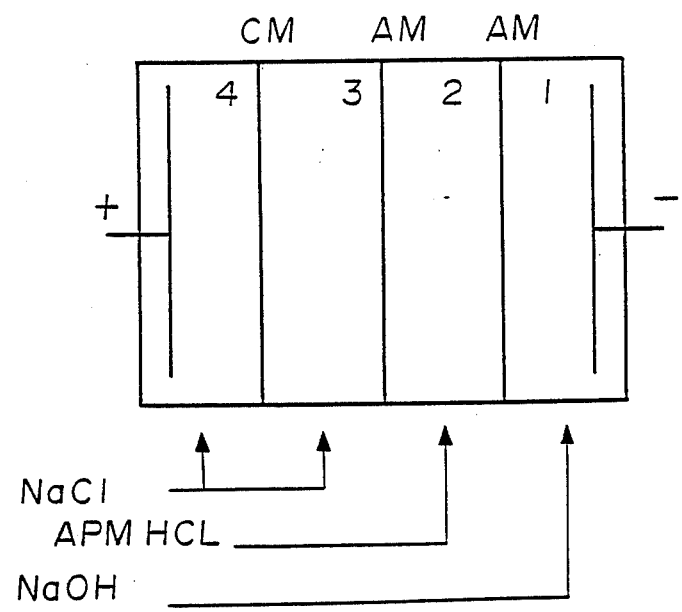

In the drawings:

FIGS. 1, 2 and 3 are schematic views illustrating different embodiments of the electrolytic process of the present invention.

Now, the present invention will be described in detail.

Ion species of the inorganic acid present as impurities in the dipeptide ester vary depending upon the process for the preparation. For example, they may be $Cl^-$ ions when the solution is acidified with hydrochloric acid. Likewise, they may be $NO_3^-$ ions when the solution is acidified with nitric acid. The method of the present invention is effective also in the case of inorganic anions such as phosphoric acid ions or sulfuric acid ions.

FIG. 1 schematically illustrates the principle of the present invention.

Namely, FIG. 1 illustrates an embodiment wherein $Cl^-$ ions are substituted by $OH^-$ ions by an electrolytic anion exchange method by supplying an aqueous a-APM solution containing an inorganic acid to an electrolytic cell devided by two anion exchange membranes into three compartments.

Reference numeral 1 indicates the electrolytic cell, each of numerals 2 and 3 indicates the anion exchange membrane (AM), numeral 4 indicates an anode, numeral 5 indicates a cathode, numeral 6 indicates an anode compartment, numeral 7 indicates a central compartment, and numeral 8 indicates a cathode compartment.

Into the central compartment 7, the aqueous α-APM solution containing the inorganic acid is supplied, a sodium chloride solution is supplied to the anode compartment 6, and a sodium hydroxide solution is supplied to the cathode compartment 8.

When the electrolytic reaction is initiated, chlorine gas is generated from the anode 4, and hydrogen gas is generated from the cathode 5.

Through the anion exchange membrane 3, $OH^-$ ions are transferred from the cathode compartment 8 to the central compartment 7, and through the anion exchange membrane 2, $Cl^-$ ions are transferred from the central compartment 7 to the anode compartment 6.

In accordance with the principle as described above, the removal of anions can be conducted at the same time as the neutralization.

The solution to be supplied to the cathode compartment may be an aqueous solution of an alkali metal such as NaOH, KOH or LiOH, an aqueous solution of an alkaline earth metal such as $Ca(OH)_2$ or $Mg(OH)_2$, or an aqueous electrolyte solution containing them. The aqueous solution to be supplied to the anode compartment may be an aqueous solution of an alkali metal such as NaCl, KCl or LiCl, an aqueous solution of an alkaline earth metal such as $MgCl_2$ or $CaCl_2$, an aqueous electrolyte solution containing them, or an aqueous solution containing an inorganic acid such as hydrochloric acid, sulfuric acid or phosphoric acid. In the case where an inorganic acid is used, the reverse diffusion of protons takes place, and it is preferred to use an aqueous electrolyte solution of other than inorganic acids, particularly an aqueous electrolyte solution containing $Cl^-$ ions which is hardly susceptible to the decomposition of water at the anode. The anode and the cathode of the electrolytic cell to be used in the present invention, may be made of conventional electrode materials.

To adapt them for the electrolytic process intended for the purification of α-APM, electrode materials which are inexpensive, exhibit a constant voltage and have excellent corrosion resistance, are suitably selected.

With respect to such electrode materials, for example, as the anode, an electrode obtained by coating a platinum group metal such as Pt, Ir or Rh and/or an oxide of a platinum group metal on the surface of a corrosion resistant substrate such as Ti, Ta, Zn or Nb, may be employed, and as the cathode, a metal such as Fe, Ni or Cu or an alloy thereof, or an electrode having a substance showing an overvoltage (such as Raney nickel) coated on its surface, may be employed.

In the electrolytic process intended for the purification of α-APM of the present invention, the electrolytic cell usually comprises three compartments i.e. an anode compartment, a central compartment and a cathode compartment. However, a multi-compartment type other than the three-compartment type may be selected, and it is also possible to conduct the electrolytic process with excellent efficiency by using a laminated cell.

The temperature for electrolysis may be from room temperature to 100° C., preferably from 10° to 80° C. If the temperature for electrolysis is high, the electrolytic voltage can be maintained at a low level. The solubility of α-APM in water is very small, and the solubility can be raised by raising the temperature. However, if the temperature for electrolysis is 80° C. or higher, α-APM tends to chemically change into DKP, whereby the yield of α-APM decreases.

The ion exchange membranes are required to have adequate durability within the above-mentioned temperature range. From such a viewpoint, fluorinated anion exchange membranes made of a copolymer having repeating units of the formula:

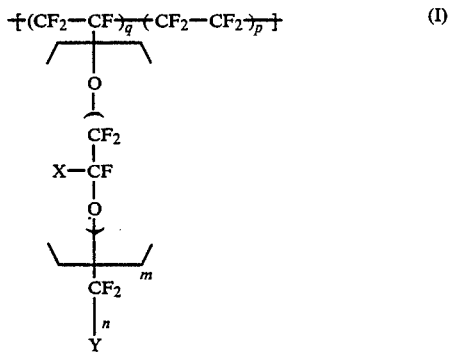

(I)

wherein X is F or CF$_3$, Y is a group involving a quaternary ammonium group, l is an integer of from 0 to 5, m is 0 or 1, n is an integer of from 1 to 5, and each of p and q is a positive number and the ratio of p/q is from 2 to 16, are preferably used.

Further, it is preferred to employ fluorinated anion exchange membranes wherein the group involving quaternary ammonium group in the above formula I has the formula:

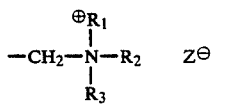

wherein each of $R_1$, $R_2$ and $R_3$ is a lower alkyl group, provided that $R_1$ and $R_2$ may together form a tetramethylene group or a pentamethylene group, $Z^\ominus$ is a halogen anion, $Bf_4^-$, $SbCl_6^-$, $R_5CO_2^-$, wherein $R_5$ is a lower alkyl group, a substituted or unsubstituted phenyl group or a lower perfluorocarbon alkyl group,

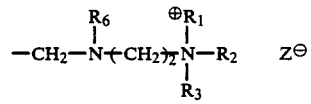

wherein $R_6$ is a hydrogen atom or a lower alkyl group, and $Z^\ominus$, $R_1$, $R_2$ and $R_3$ are as defined above,

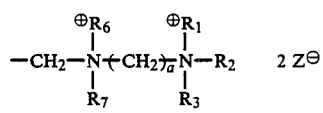

wherein each of $R_6$ and $R_7$ is a hydrogen atom or a lower alkyl group, a is an integer of from 3 to 6, and $Z^\ominus$, $R_1$, $R_2$ and $R_3$ are as defined above, or

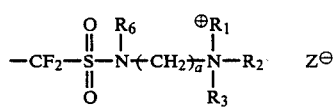

wherein a is an integer of from 2 to 6, and $R_1$, $R_2$, $R_3$, $R_6$ and $Z^\ominus$ are as defined above.

As such fluorinated anion exchange membranes, polymer membranes having the following structures may be mentioned as specific examples.

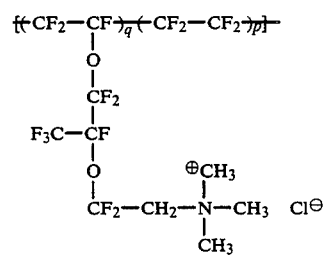

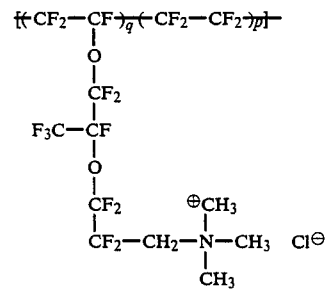

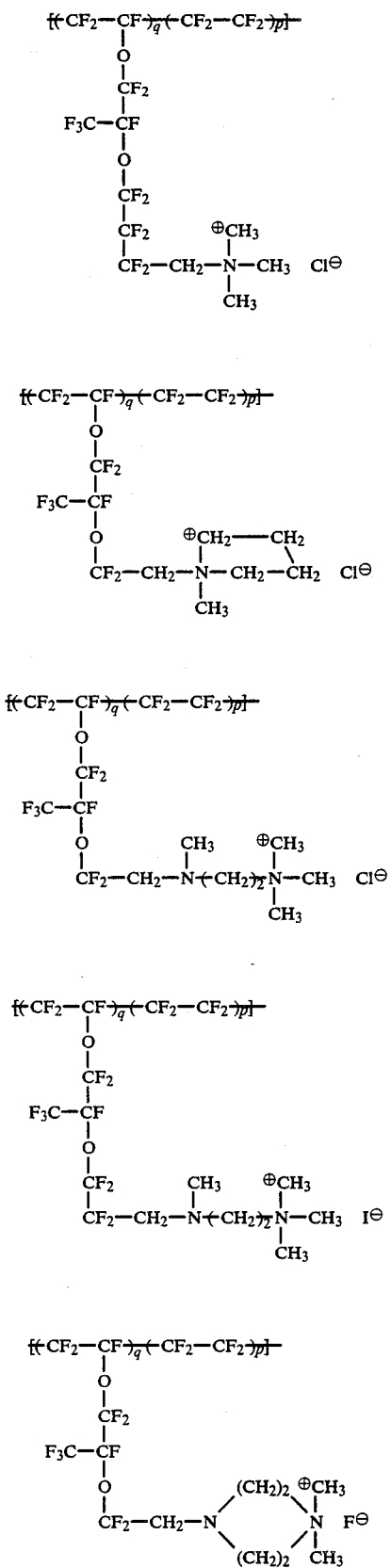
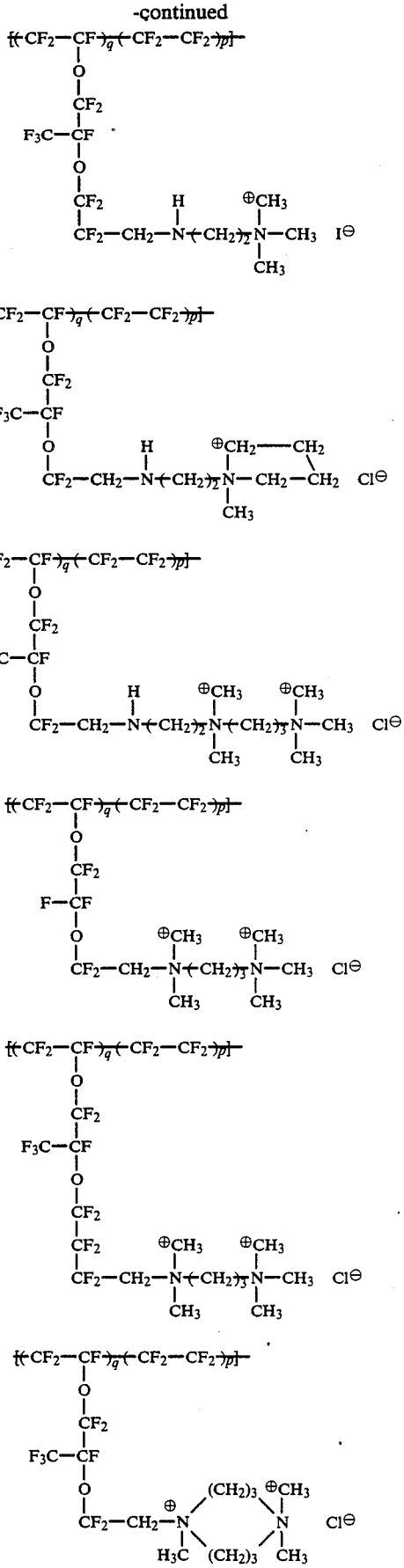

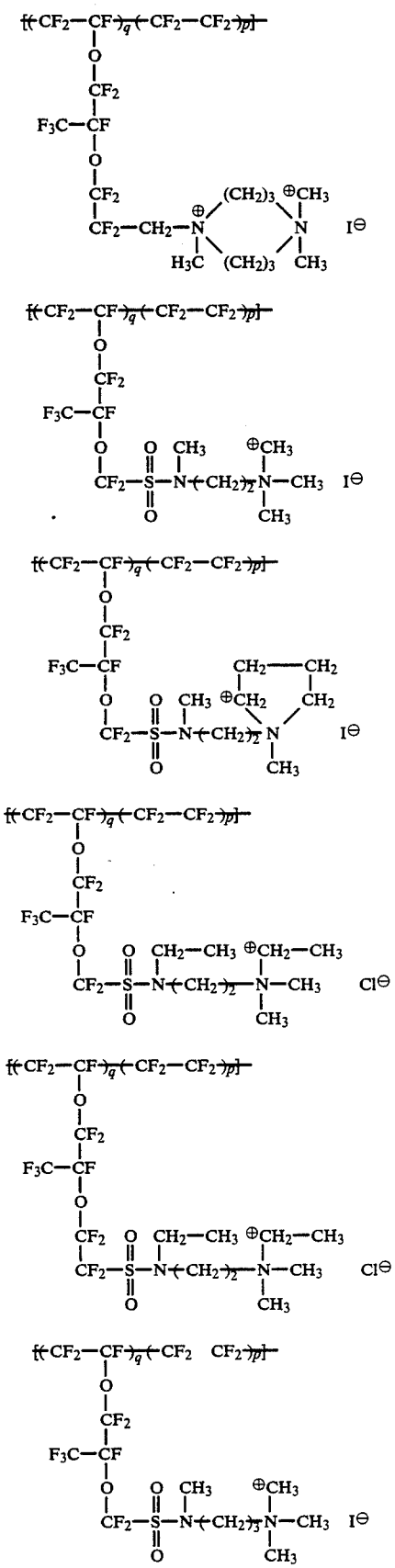
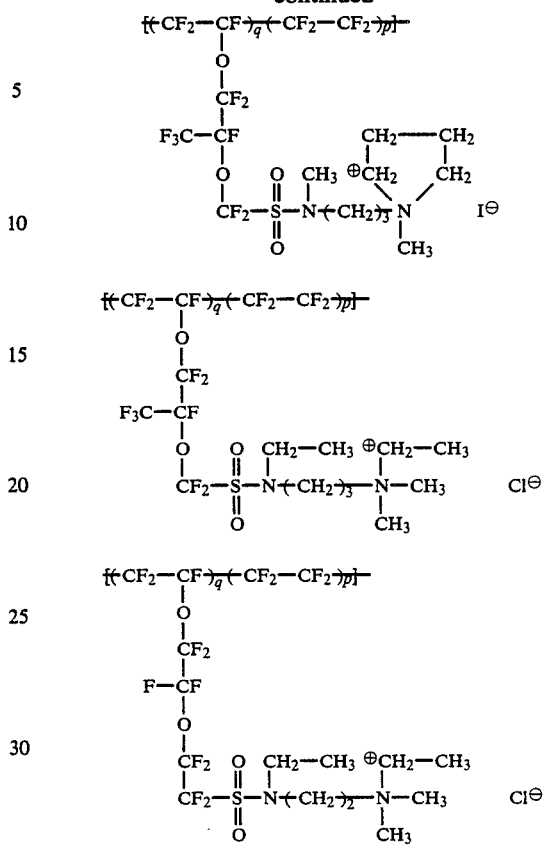

It is preferred to employ fluorinated anion exchange membranes having a group involving a quaternary ammonium as illustrated above.

The ion exchange capacity of the fluorinated anion exchange membranes to be used in the present invention may be within a range of from 0.16 to 3.0 meq/g dry resin, preferably within a range of from 0.5 to 2.8 meg/g dry resin. If the ion exchange capacity is less than the above range, the membrane resistance tends to be high, the electorolytic voltage tends to be high, and the cost for the electric power increases. On the other hand, if the ion exchange capacity exceeds the above range, there will be a problem such as the swelling or disintegration of the membranes, which hinders a stabilized electrolytic operation.

The thickness of the fluorinated anion exchange membranes to be used in the present invention may usually be within a range of from 40 to 500 μm, preferably within a range of from 100 to 300 μm.

In the present invention, the recovery rate of a-APM is 95% or higher when fluorinated anion exchange membranes having a uniform ion exchange capacity are employed. In order to improve the recovery rate of α-APM to a level close to 100%, it is preferred to employ fluorinated anion exchange membranes having the ion exchange capacity varied from one side to the other side.

The fluorinated anion exchange membranes wherein the ion exchange capacity varies from one side to the other side, preferably have a ratio of the ion exchange capacities within a range of from 1.1 to 1.6, more preferably within a range of from 1.3 to 4.0. If the ratio of the ion exchange capacities is less than the above range, the recovery rate of a-APM is 95% or higher. In order to improve the recovery rate of a-APM to a level close to 100%, it is advisable to adopt the ratio of the ion exchange capacities within the above-mentioned range. If the ratio of the ion exchange capacities exceeds the above range, it is possible that the electrical resistance of the membranes increases.

As described in the foregoing, according to the method of the present invention, the decomposition of the dipeptide ester can be suppressed, and the removal of an inorganic acid can efficiently be carried out without substantial leakage, and thus the purification of a dipeptide ester by an electrolytic process far superior to the conventional method can be realized as an industrial process.

Now, the present invention will be described in further detail with reference to Examples. However, it should be understood that the present invention is by no means restricted to such specific Examples

EXAMPLE 1

An electrolytic ion exchange method was conducted to obtain pure α-APM from an aqueous solution containing 3.5% by weight of o-L-aspartyl-L-phenylalanine methyl ester (α-APM) and about 300 ppm of Cl⁻ ions.

The electrolytic cell was a three-compartment type electrolytic cell as shown in FIG. 1. As the anode, an electrode having a noble metal oxide coated on a Ti expanded metal substrate was used, and as the cathode, a Ni expanded metal was used.

The electrode surface area for each of the anode and cathode was 0.1 dm², and the distance between the anode and the cathode was 7.9 mm.

As the anion exchange membrane for partitioning the anode compartment and the central compartment, a fluorinated anion exchange membrane (ion exchange capacity: 1.4 meq/g dry resin, thickness: 175 μm) having the following structure:

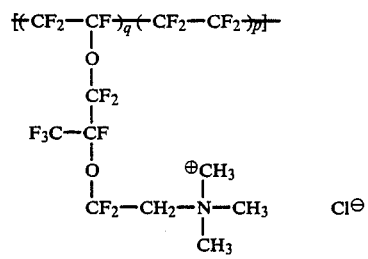

was used, and as the anion exchange membrane for partitioning the anode compartment and the central compartment, a fluorinated anion exchange membrane (ion exchange capacity: 0.91 meq/g dry resin, thickness: 180 μm) having the following structure:

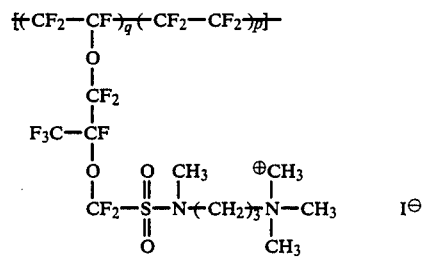

was used.

To the anode compartment, a 0.5 N NaCl aqueous solution was supplied. To the central compartment, the aqueous solution containing 3.5% by weight of α-L-aspartyl-L-phenylalanine methyl ester (α-APM) and 322 ppm of Cl⁻ ions, was supplied. To the cathode compartment, a 0.5 N NaOH aqueous solution was supplied.

The electrolysis was conducted at a current density of 1.2 A/dm² at 60° C., whereby the electrolytic voltage was 6.1 V.

As the electrolysis is continued, α-APM hydrochloride in the α-APM solution changes to α-APM, and the pH of the aqueous o-APM solution in the central compartment increases to a level close to the isoelectric point, whereby the electrical conductivity lowers.

Accordingly, the electrolytic voltage increases. When the pH in the central compartment exceeded 5.1, the electrolysis was stopped, whereby the removal rate of Cl⁻ ions in the central compartment i.e. the electrolytic ion exchange rate was 64.9%, the recovery rate of α-APM was 96.5%, and the current efficiency was 87.6%. Further, after the electrolysis, the amounts of α-APM in the anode compartment and the cathode compartment were measured, whereby leakage of 0.007% of a-APM in the anode compartment was detected by liquid chromatography, and DKP and AP formed by the thermal decomposition of α-APM were detected in amounts of 0.003% and 0.004%, respectively. No substantial leakage to the cathode compartment was detected. The current efficiency of 87.6% is considered to indicate that as Cl2 gas formed in the anode compartment, H2O in the anolyte was decomposed to produce O2 gas, and at the same time, H+ ions were formed in the anolyte, whereupon the H+ ions were transferred through the anion exchange membrane to the central compartment to neutralize OH⁻ ions which were transferred to the central compartment through the other anion exchange membrane.

EXAMPLE 2

The same α-APM solution as used in Example 1 was electrolyzed in a three-compartment type electrolytic cell as shown in FIG. 1 by using the same electrodes as used in Example 1, whereby the electrode surface area of each of the anode and cathode was 0.1 dm²,and the distance between the anode and cathode was 7.9 mm.

As the anion exchange membrane for partitioning the cathode compartment and the central compartment, a fluorinated anion exchange membrane (wherein the ion exchange capacity varies from one side to the other side i.e. ion exchange capacity on the catholyte side: 0.9 meq/g dry resin, ion exchange capacity on the central compartment side: 0.6 meq/g dry resin, thickness: 180 μm) having the following structure:

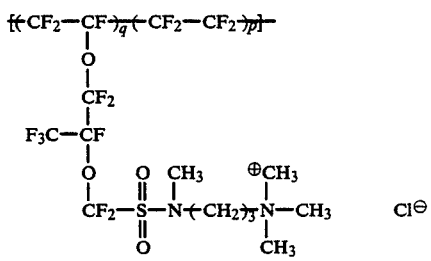

was used.

As the anion exchange membrane for partitioning the central compartment and the anode compartment, a fluorinated anion exchange membrane (wherein the ion exchange capacity varies from one side to the other side i.e. ion exchange capacity on the central compartment side: 0.6 meq/g dry resin, ion exchange capacity on the anode compartment side: 1.4 meq/g dry resin, thickness: 175 μm) having the following structure:

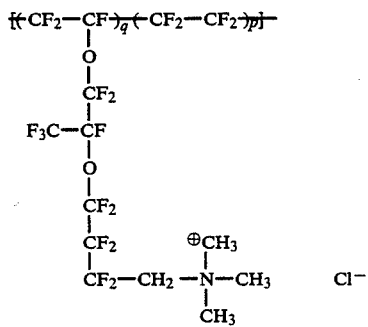

was used.

To the anode compartment, a 0.5 N NaCl aqueous solution was supplied. To the central compartment, an aqueous solution containing 3.5% by weight of α-L-aspartyl-L-phenylalanine methyl ester (α-APM) and 311 ppm of Cl⁻ ions, was supplied. To the cathode compartment, a 0.5 N NaOH aqueous solution was supplied.

The electrolysis was conducted at a current density of 2.0 A/dm² at 60° C., whereby the electrolytic voltage was 7.0 V.

As the electrolysis is continued, α-APM hydrochloride in the α-APM solution changes to α-APM, and the pH of the aqueous α-APM solution in the central compartment increases simultaneously to a level close to the isoelectric point, whereby the electrical conductivity tends to be low.

Accordingly, the electrolytic voltage increases. When the pH of the central compartment exceeded 5.1, the electrolysis was stopped, whereby the removal rate of Cl⁻ ions in the central compartment i.e. the electrolytic ion exchange rate was 82.7%, the recovery rate of α-APM was 8.5%, and the current efficiency was 88.5%. Further, the amounts of α-APM in the anode compartment and the cathode compartment were measured, whereby leakage of 0.006% of α-APM was detected by liquid chromatography, DKP formed by the thermal decomposition of α-APM was 0.002%, and no substantial AP was detected. The current efficiency of 82.7% is considered to indicate that as Cl₂ gas was formed in the anode compartment, H₂O in the anolyte was decomposed to produce O₂ gas, and at the same time, H⁺ ions were formed in the anolyte, and the H⁺ ions were transferred to the central compartment through the anion exchange membrane to neutralize OH⁻ ions which were transferred to the central compartment through the other anion exchange membrane. As compared with Example 1, the current efficiency was good, and the recovery rate of α-APM was improved. This is considered to be attributable to the use of the anion exchange membrane wherein the ion exchange capacity varies from one side to the other side.

EXAMPLE 3

The same α-APM solution as used in Example 1 was electrolyzed in a six-compartment type electrolytic cell as shown in FIG. 2, whereby the same electrodes as used in Example 1 were employed, and the electrode surface area of each of the anode and cathode was 0.1 dm², and the distance between the anode and cathode was 17.5 mm.

As the anion exchange membrane for partitioning the cathode compartment 1 and the compartment 2, a fluorinated anion exchange membrane (wherein the ion exchange capacity varies from one side to the other side i.e. ion exchange capacity on the catholyte side (compartment 1): 0.9 meq/g dry resin, ion exchange capacity on the compartment 2 side: 0.6 meq/g dry resin, thickness: 180 μm) having the following structure:

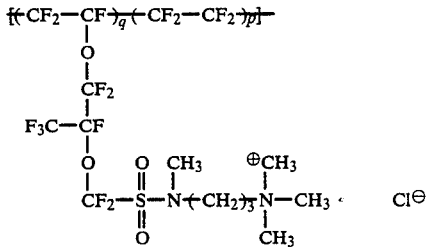

was used.

As the anion exchange membrane for partitioning the compartments 2 and 3, a fluorinated anion exchange membrane (wherein the ion exchange capacity varies from one side to the other i.e. ion exchange capacity on the compartment 2 side: 0.6 meq/g dry resin, ion exchange capacity on the compartment 3 side: 0.9 meq/g dry resin, thickness: 180 μm) having the following formula:

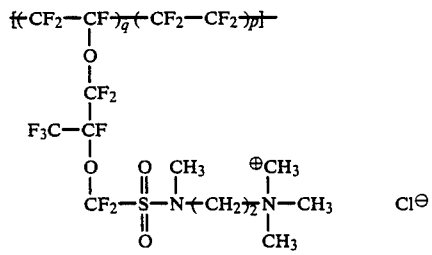

was used.

As a cation exchange membrane for partitioning the compartments 3 and 4, Nafion 423 as a conventional commercially available fluorinated cation exchange membrane, was used.

As the anion exchange membrane for partitioning the compartments 4 and 5, a fluorinated anion exchange membrane (wherein the ion exchange capacity varies from one side to the other side i.e. ion exchange capacity on the compartment 4 side: 0.9 meq/g dry resin, ion exchange capacity on the compartment 5 side: 0.6 meq/g dry resin, thickness: 180 μm) having the following structure:

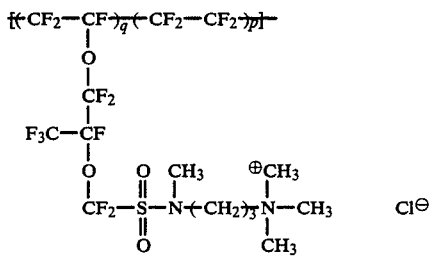

was used.

As the anion exchange membrane for partitioning the compartment 5 and the anode compartment 6, a fluorinated anion exchange membrane (wherein the ion exchange capacity varies from one side to the other i.e. ion exchange capacity on the compartment 5 side: 0.6 meq/g dry resin, ion exchange capacity on the compartment 6 side: 1.4 meq/g dry resin, thickness: 175μ) having the following structure:

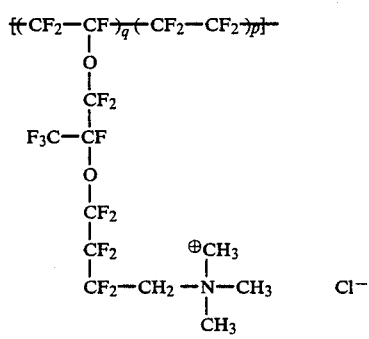

was used.

To the anode compartment 6 and the compartment 3, a 0.5 N NaCl aqueous solution was supplied. To the cathode compartment 1 and the compartment 4, 0.5 N NaOH was supplied. To the compartments 2 and 5, an aqueous solution containing 3.5% of α-L-aspartyl-L-phenylalanine methyl ester (α-APM) and its hydrochloride, was supplied.

The electrolysis was conducted at a current density of 2 A/dm² at 60° C., whereby the electrolytic voltage was 14.6 V.

As the electrolysis is continued, α-APM hydrochloride in the solution changes to α-APM, and the pH of the aqueous o-APM solution in the central compartment increases to a level close to the isoelectric point, whereby the electrical conductivity decreases.

When the pH of the aqueous α-APM solution exceeded 5.1, the electrolysis was stopped, whereby the removal rate of Cl⁻ ions in the compartments 2 and 5 i.e. the electrolytic ion exchange rate, was 77%, the recovery rate of a-APM was 98.3%, and the current efficiency was 87.6%.

After the electrolysis, the amounts of α-APM in the anode compartment and the cathode compartment were measured, whereby 0.006% of α-APM, 0.019% of DKP and 0.003% of AP were detected in the anode compartment by chromatography, and no substantial presence of such substances detected in the cathode compartment.

EXAMPLE 4

An electrolytic ion exchange method was conducted to obtain pure α-APM from an aqueous solution containing 3.5% by weight of α-L-aspartyl-L-phenylalanine methyl ester hydrochloride (α-APM.HCl). The electrolysis was conducted by using a three-compartment type electrolytic cell as shown in FIG. 1 and the same electrodes as used in Example 1, whereby the electrode surface area of each of the anode and cathode was 0.1 dm², and the distance between the anode and cathode was 7.9 mm.

As the anion exchange membrane for partitioning the anode compartment and the central compartment, a fluorinated anion exchange membrane (ion exchange capacity: 1.4 meq/g dry resin, thickness: 175 μm) having the following formula:

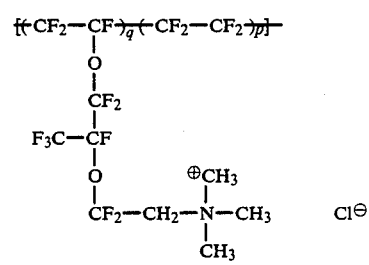

was used. As the anion exchange membrane for partitioning the cathode compartment and the central compartment, a fluorinated anion exchange membrane (ion exchange capacity: 0.91 meq/g dry resin, thickness: 180 μm) having the following structure:

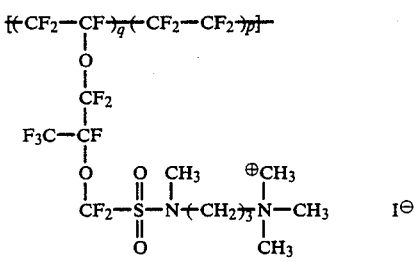

was used.

To the anode compartment, a 0.5 N NaCl aqueous solution was supplied., To the central compartment, an aqueous solution containing 3.5% by weight of α-L-aspartyl-L-phenylalanine methyl ester hydrochloride (α-APM.HCl) was supplied. To the cathode compartment, a 0.5 N NaOH aqueous solution was supplied.

The electrolysis was conducted at a current density of 20.0 A/dm² at 60° C., whereby the electrolytic voltage was 8.5 V.

As the electrolysis is continued, α-APM hydrochloride in the aqueous solution changes to α-APM, and the pH of the aqueous solution in the central compartment increases to a level close to the isoelectric point, whereby the electrical conductivity decreases.

Accordingly, the electrolytic voltage increases. When the pH in the central compartment exceeded 5.1, the electrolysis was stopped, whereby the removal rate of Cl⁻ ions in the central compartment i.e. the electrolytic ion exchange rate, was 98.5%, the recovery rate of α-APM was 96.3%, and the current efficiency was 89.6%.

After the electrolysis, the amounts of α-APM in the anode compartment and the cathode compartment were measured, whereby leakage of 0.005% of α-APM in the anode compartment was detected by liquid chromatography, and DKP and AP formed by the thermal decomposition of α-APM were detected in amounts of 0.012% and 0.013%, respectively. No substantial leakage to the cathode compartment was detected.

EXAMPLE 5

An electrolytic ion exchange method was conducted to obtain pure α-APM from an aqueous solution containing 0.5% by weight of α-L-aspartyl-L-phenylalanine methyl ester hydrochloride (α-APM.HCl).

The electrolysis was conducted by using a four-compartment electrolytic cell as shown in FIG. 3 and the same electrodes as used in Example 1. The electrode surface area of each of the anode and the cathode was 0.1 dm², and the distance between the anode and cathode was 11.1 mm.

As the anion exchange membrane for partitioning the cathode compartment 1 and the intermediate compartment 2, RAIPORE R-4035 was used. As the anion exchange membrane for partitioning the intermediate compartments 2 and 3, RAIPORE R-4035 was used. As the anion exchange membrane protective layer on the anode side for partitioning the intermediate compartments 3 and 4, Nafion 423 was used.

To the anode compartment 4, a 0.5 N NaCl aqueous solution was supplied. To the intermediate compartment 3, a 0.5 N NaCl aqueous solution was supplied. To the intermediate compartment 2, an aqueous solution containing 3.5% by weight of α-L-aspartyl-L-phenylalanine methyl ester hydrochloride (α-APM.HCl) was supplied. To the cathode compartment 1, a 0.5 N NaOH aqueous solution was supplied.

The electrolysis was conducted at a current density of 20.0 A/dm² at 60° C., whereby the electrolytic voltage was 9.9 V.

As the electrolysis is continued, α-APM hydrochloride in the aqueous solution changes to α-APM, and the pH of the solution increases to a level close to the isoelectric point, whereby the electrical conductivity decreases.

Accordingly, the electrolytic voltage increases. When the pH of the intermediate compartment 2 exceeded 5.1, the electrolysis was stopped, whereby the removal rate of Cl⁻ ions in the intermediate compartment i.e. the electrolytic ion exchange rate, was 94.5%, the recovery rate of α-APM was 73.3%, and the current efficiency was 66.4%. After the electrolysis, the amounts of α-APM in the anode compartment and the cathode compartment were measured, whereby leakage of 1.125% of α-APM was detected by liquid chromatography, and DKP and AP formed by the thermal decomposition of a-APM were detected in amounts of 0.885% and 0.133%, respectively. The only leakage to the cathode compartment was 0.107% of DKP.

We claim:

1. A method for purifying a dipeptide ester by electrolysis in an electrolytic cell comprising an anode compartment, a cathode compartment and a central compartment partitioned by anion exchange membranes, which comprises supplying an aqueous dipeptide ester solution containing an inorganic acid to the central compartment defined by said anion exchange membranes, an aqueous solution containing a basic substance or an aqueous electrolyte solution containing a basic substance to the cathode compartment and an aqueous electrolyte solution to the anode compartment, supplying hydroxyl ions from the cathode compartment to the central compartment through the anion exchange membrane to neutralize the aqueous dipeptide ester solution containing the inorganic acid and removing anions of the inorganic acid in the aqueous dipeptide ester solution from the central compartment to the anode compartment through the anion exchange membrane.

2. The method according to claim 1, wherein the inorganic acid is a hydrogen halide acid, nitric acid, phosphoric acid or sulfuric acid.

3. The method according to claim 1, wherein the dipeptide ester is α-aspartyl-L-phenylalanine methyl ester.

4. The method according to claim 1, wherein the anion exchange membranes are fluorinated anion exchange membranes made of a copolymer having repeating units of the formula:

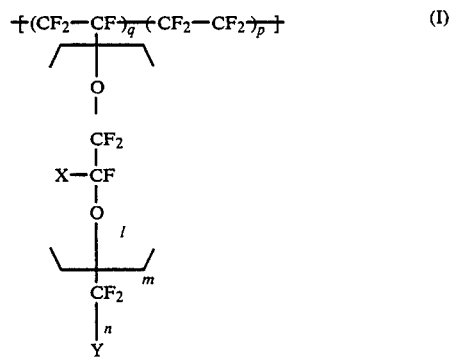

wherein X is F or CF₃, Y is a group involving a quaternary ammonium group, l is an integer of from 0 to 5, m is 0 or 1, n is an integer of from 1 to 5, and each of p and q is a positive number and the ratio of p/q is from 2 to 16.

5. The method according to claim 4, wherein the group involving a quaternary ammonium group has the formula:

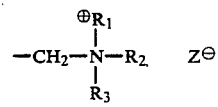

wherein each of $R_1$, $R_2$ and $R_3$ is a lower alkyl group, provided that $R_1$ and $R_2$ may together form a tetramethylene group or a pentamethylene group, $Z^\ominus$ is a halogen anion, $BF_4^-$, $SbCl_6^-$, $R_5SO_3^-$, $R_5CO_2^-$, wherein $R_5$ is a lower alkyl group, a substituted or unsubstituted phenyl group or a lower perfluorocarbon alkyl group,

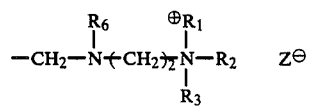

wherein $R_6$ is a hydrogen atom or a lower alkyl group, and $Z^\ominus$, $R_1$, $R_2$ and $R_3$ are as defined above,

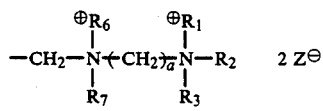

wherein each of $R_6$ and $R_7$ is a hydrogen atom or a lower alkyl group, a is an integer of from 3 to 6, and $Z^\ominus$, $R_1$, $R_2$ and $R_3$ are as defined above, or

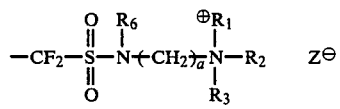

wherein a is an integer of from 2 to 6, and $R_1$, $R_2$, $R_3$, $R_6$ and $Z^\ominus$ are as defined above.

6. The method according to claim 1, wherein the electrolytic cell is partitioned into at least three compartments by the anion exchange membranes.

7. The method according to claim 1, wherein the basic substance is an alkali metal hydroxide, an alkaline earth metal hydroxide, ammonium hydroxide or an organic amine.

8. The method according to claim 1, wherein the aqueous electrolyte solution is an aqueous solution of an alkali metal salt or an alkaline earth metal salt, or an aqueous solution of an inorganic acid.

9. The method according to claim 1, wherein the temperature for electrolysis is within a range of from 10 to 80° C.

10. The method according to claim 4, wherein each of the fluorinated anion exchange membranes has its ion exchange capacity varied from one side to the other side.

* * * * *